(12) United States Patent
Dusan

(10) Patent No.: US 10,531,808 B2
(45) Date of Patent: *Jan. 14, 2020

(54) METHOD OF DETECTING THE WEARING LIMB OF A WEARABLE ELECTRONIC DEVICE

(71) Applicant: Apple Inc., Cupertino, CA (US)

(72) Inventor: Sorin V. Dusan, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/059,851

(22) Filed: Aug. 9, 2018

(65) Prior Publication Data

US 2018/0344189 A1 Dec. 6, 2018

Related U.S. Application Data

(63) Continuation of application No. 15/130,616, filed on Apr. 15, 2016, now Pat. No. 10,045,708, which is a
(Continued)

(51) Int. Cl.
*A61B 5/0452* (2006.01)
*A61B 5/00* (2006.01)
(Continued)

(52) U.S. Cl.
CPC .......... *A61B 5/0452* (2013.01); *A61B 5/0006* (2013.01); *A61B 5/0404* (2013.01);
(Continued)

(58) Field of Classification Search
CPC ............................ A61B 5/0452; A61B 5/0006
(Continued)

(56) References Cited

U.S. PATENT DOCUMENTS 5,483,261 A 1/1996 Yasutake
5,488,204 A 1/1996 Mead et al.
(Continued)

FOREIGN PATENT DOCUMENTS

DE 10-2009-012352 A1 9/2012
EP 0 712 605 A1 5/1996
(Continued)

OTHER PUBLICATIONS

Balazs, G. et al. (Sep. 19, 2004). "Intelligent Cardiac Telemonitoring System," Computers in Cardiology, *IEEE*, pp. 745-748.
(Continued)

*Primary Examiner* — Nadia A Mahmood
(74) *Attorney, Agent, or Firm* — Brownstein Hyatt Farber Schreck, LLP

(57) ABSTRACT

A wearable device configured to acquire and process electrocardiographic measurements, detect lead inversion and correct the acquired measurements for lead inversion is provided. In one example, the wearable device can detect lead inversion by first assessing whether the P-wave of a given electrocardiographic measurement has a negative amplitude, and if the P-wave is found to be negative, the device can determine if the magnitude of the R-wave is smaller than the maximum of the magnitudes of the S-wave and the Q-wave. In another example, the device can be put through an enrollment procedure in which electrocardiographic measurements are taken with the device being worn at known locations on the body. Once the enrollment procedure is completed, when the device is being used, any electrocardiographic results obtained can be compared against the measurements taken during the enrollment phase, and the location of the device on the body can be determined.

20 Claims, 11 Drawing Sheets

Related U.S. Application Data continuation of application No. 14/915,218, filed as application No. PCT/US2013/056681 on Aug. 26, 2013, now abandoned.

(51) Int. Cl.

| | |
|---|---|
| *A61B 5/0404* | (2006.01) |
| *G06K 9/00* | (2006.01) |
| *A61B 5/04* | (2006.01) |
| *A61B 5/0408* | (2006.01) |
| *G16H 40/63* | (2018.01) |

(52) U.S. Cl.
CPC ........ *A61B 5/0408* (2013.01); *A61B 5/04012* (2013.01); *A61B 5/681* (2013.01); *A61B 5/6824* (2013.01); *A61B 5/6841* (2013.01); *A61B 5/7246* (2013.01); *A61B 5/7264* (2013.01); *G06K 9/00536* (2013.01); *A61B 2505/07* (2013.01); *G16H 40/63* (2018.01)

(58) Field of Classification Search
USPC ................................. 600/509, 544
See application file for complete search history.

(56) References Cited

U.S. PATENT DOCUMENTS

| | | | |
|---|---|---|---|
| 5,640,966 A | 6/1997 | Heden et al. |
| 5,825,352 A | 10/1998 | Bisset et al. |
| 5,835,079 A | 11/1998 | Shieh |
| 5,880,411 A | 3/1999 | Gillespie et al. |
| 6,188,391 B1 | 2/2001 | Seely et al. |
| 6,282,440 B1 | 8/2001 | Brodnick et al. |
| 6,310,610 B1 | 10/2001 | Beaton et al. |
| 6,323,846 B1 | 11/2001 | Westerman et al. |
| 6,690,387 B2 | 2/2004 | Zimmerman et al. |
| 7,015,894 B2 | 3/2006 | Morohoshi |
| 7,184,064 B2 | 2/2007 | Zimmerman et al. |
| 7,663,607 B2 | 2/2010 | Hotelling et al. |
| 8,479,122 B2 | 7/2013 | Hotelling et al. |
| 2006/0197753 A1 | 9/2006 | Hotelling |
| 2007/0232946 A1 | 10/2007 | Field et al. |

FOREIGN PATENT DOCUMENTS

| | | |
|---|---|---|
| GB | 2 438 589 A | 5/2007 |
| JP | 2000-163031 A | 6/2000 |
| JP | 2002-342033 A | 11/2002 |
| WO | WO-91/00052 A1 | 1/1991 |

OTHER PUBLICATIONS

Final Office Action dated Oct. 10, 2017, for U.S. Appl. No. 15/130,616, filed Apr. 15, 2016, six pages.

Hyung, W.N. et al. (Aug. 28, 2012). "A Preliminary Study of the Effect of Electrode Placement in Order to Define a Suitable Location for Two Electrodes and Obtain Sufficiently Reliable ECG Signals When Monitoring with Wireless System," *The Effecto of Applied Compressive Loading on Tissue-Engineered Cartilage Constructs Cultures with TGF-Beta3, IEEE*, pp. 2124-2127.

International Search Report dated May 12, 2014, for PCT Patent Application No. PCT/US2013/056681, filed Aug. 26, 2013, four pages.

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Non-Final Office Action dated Jan. 26, 2017, for U.S. Appl. No. 15/130,616, filed Apr. 15, 2016, five pages.

Notice of Allowance dated Apr. 20, 2018, for U.S. Appl. No. 15/130,616, filed Apr. 15, 2016, nine pages.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

METHOD OF DETECTING THE WEARING LIMB OF A WEARABLE ELECTRONIC DEVICE

CROSS-REFERENCE TO RELATED APPLICATIONS

This application is a continuation of U.S. patent application Ser. No. 15/130,616, filed Apr. 15, 2016, published on Aug. 11, 2016 as U.S. Publication No. 2016-0228025, which is a continuation of U.S. patent application Ser. No. 14/915, 218, with an international filing date of Aug. 26, 2013, which is a National Phase application under 35 U.S.C. § 371 of International Application No. PCT/US2013/056681, filed Aug. 26, 2013, the contents of which are hereby incorporated by reference in their entirety for all intended purposes.

FIELD OF DISCLOSURE

This relates generally to wearable electrical devices that have the capability of recording electrocardiographic signals, and more particularly to detecting and correcting for inversions in electrocardiographic measurements caused by wearing the device on varying locations on the human body.

BACKGROUND OF THE DISCLOSURE

Computing devices such as desktop computers, laptop computers, mobile phones, smartphones, watches, tablet devices and portable multimedia players are popular. These computing devices can be used for performing a wide variety of tasks, from the simple to the most complex. As an example, some portable computing devices can have electrocardiographic functionality with various kinds or types of electrodes configured to be worn or attached to identified locations on the human body for the purpose of making measurements of the electrical activity of the human heart.

A portable computing device can be fashioned into a wearable accessory that can be worn on the body. Examples of a wearable device can include a watch, a ring, a pendant, a brooch, a wrist-band or wrist band, a pendant, a bracelet, etc. A wearable device can be affixed to a limb of the human body such as a wrist or ankle, as an example. The wearable device can be worn on the left or right wrist, or even on the right or left ankle. Since electrocardiographic measurements can depend on the electrode's relative position to the heart being measured, and since the electrodes can be affixed to the wearable device, changing the device's location from right to left, or wrist to ankle, can have an impact on the acquired electrocardiographic measurements. As an example, wearing the device on the left wrist vs. wearing the device on the right wrist can produce electrocardiographic measurements that are inverted relative to one another.

SUMMARY

This relates to a wearable device that can determine the wearing limb of the device, and if the device is being worn in such a way as to produce inverted electrocardiographic readings, can then correct the inverted readings in order to produce electrocardiographic measurements that are consistent for a given pair of limbs of the user. In one example, the wearable device can detect lead inversion by first assessing whether the P-wave of a given electrocardiographic measurement has a negative amplitude, and if the P-wave is found to be negative, the device can determine if the magnitude of the R-wave is smaller than the maximum of the magnitudes of the S-wave and the Q-wave. If both of the conditions are true, the device can determine that the electrocardiographic reading is inverted and correct for the inversion. In another example, the device can be put through an enrollment procedure in which electrocardiographic measurements are taken with the device being worn at known locations on the body. Once the enrollment procedure is completed, when the device is being used, any electrocardiographic results obtained can be compared against the measurements taken during the enrollment phase, and the location of the device on the body can be determined.

DETAILED DESCRIPTION

In the following description of examples, reference is made to the accompanying drawings which form a part hereof, and in which it is shown by way of illustration specific examples of the disclosure that can be practiced. It is to be understood that other examples can be used and structural changes can be made without departing from the scope of the examples of this disclosure.

This relates to a method of detecting lead inversion and the location of the wearing limb in an electrocardiographic measurement taken by a wearable device, and correcting the acquired measurement if it is determined that lead inversion has occurred.

Although examples disclosed herein may be described and illustrated herein in terms of the wearable devices, it should be understood that the examples are not so limited, but are additionally applicable to electrocardiographic measurements taken by non-wearable heart monitors in which electrodes are placed on the body. Furthermore, although examples may be described and illustrated herein in terms of wearable devices that can be worn on the wrists and ankles, it should be understood that the examples are also applicable to wearable devices that can be worn on the hands, wrists, legs, feet or any other part of the body.

Figure 1:
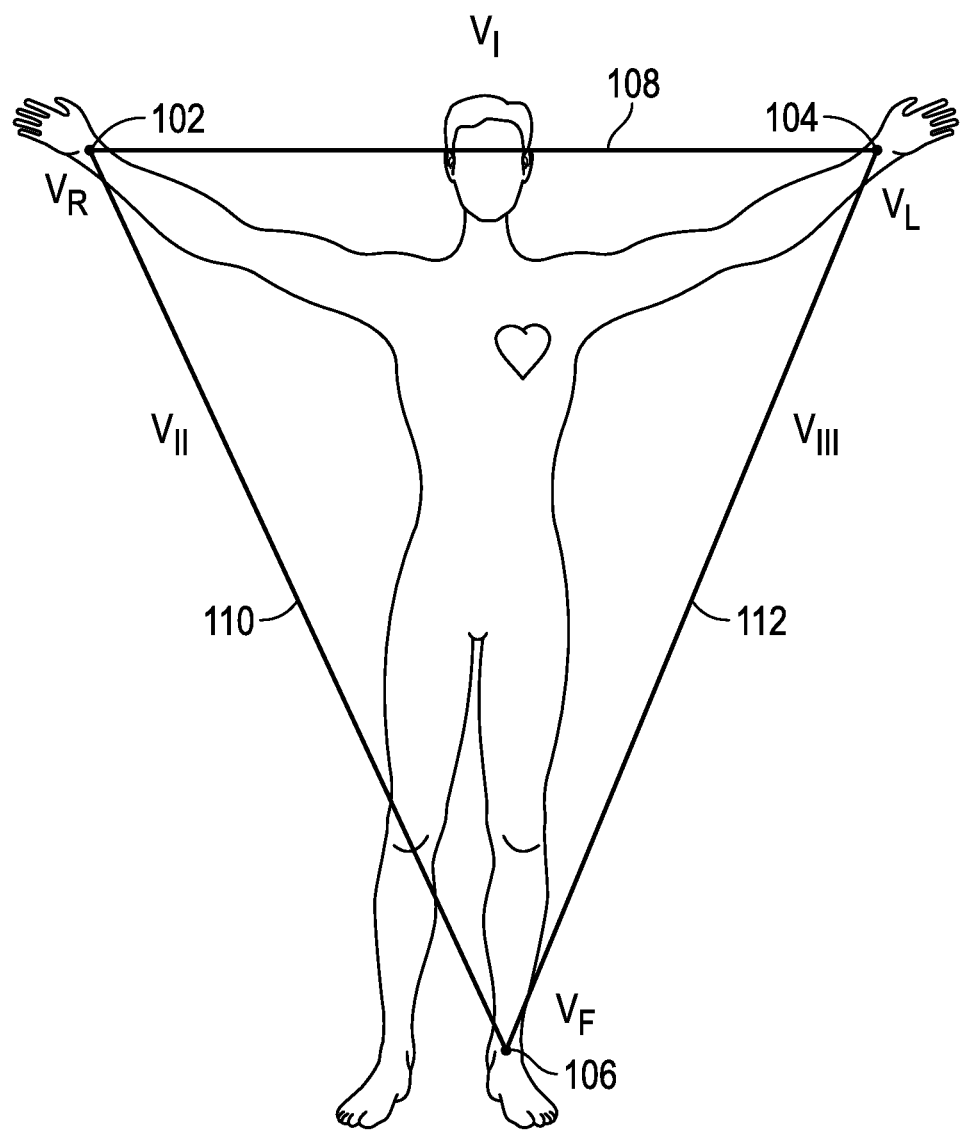
FIG. 1 illustrates various electrocardiographic lead configurations according to examples of the disclosure.

FIG. 1 illustrates various electrocardiographic lead configurations according to examples of the disclosure. In some examples, electrocardiographic electrodes (i.e., sensors that measure electrical potential at a particular location on the body) can be placed on a human body in various locations. As illustrated in FIG. 1, electrocardiographic electrodes can be placed on the right wrist (from the perspective of the patient) 102, the left wrist 104, or on the left leg 106. Placing the electrodes in this manner can form what is known in the art as Einthoven's triangle. Einthoven's triangle can have sides, 108, 110, and 112. Each side of the triangle can represent a lead configuration for taking an electrocardiographic measurement. For instance, side 108 of the triangle, known in the art as the Lead I configuration, can represent measuring the potential difference between the left wrist and the right wrist. Side 110 of the triangle, known in the art as the Lead II configuration, can represent measuring the potential difference between the left leg and the right wrist. Side 112 of the triangle, known in the art as the Lead III configuration, can represent measuring the potential difference between the left leg and the left wrist. By measuring the potential difference between any two electrodes of the three electrodes, an electrocardiographic measurement can be taken. Each lead configuration can also have two possible ways to produce measurements. For instance, the Lead I configuration 108 can measure the potential difference between the left wrist ($V_L$) and the right wrist ($V_R$). This potential difference can be expressed as the difference between the voltages measured at the right wrist and the left wrist, for example, as expressed in equation 1:

$$V_I = V_L - V_R \quad (1)$$

The $V_L$ and $V_R$ potentials can be measured with respect to a ground electrode, for example, placed on the right leg. The potential difference between the right wrist and the left wrist can also be expressed as:

$$-V_I = V_R - V_L \quad (2)$$

Equations 1 and 2 thus can be inversions of one another. This can mean that depending on which electrode is the positive electrode (i.e., the number being subtracted from) and which electrode is the negative electrode (i.e., the number being subtracted), the results can be inverted with respect to one another.

The Lead II configuration can measure the potential difference between the left leg 106 and the right wrist 102. This potential difference can be expressed as the difference between the voltages measured at the right wrist and left ankle, for example, as expressed in equation 3:

$$V_{II} = V_F - V_R \quad (3)$$

The potential difference between the right wrist and the left ankle can also be expressed as:

$$-V_{II} = V_R - V_F \quad (4)$$

Equations 3 and 4 thus can be inversions of one another. This can mean that depending on which electrode is the positive electrode and which electrode is the negative electrode, the results can be inverted with respect to one another.

The Lead III configuration can measure the potential difference between the left leg 106 and the left wrist 104. This potential difference can be expressed as the difference between the voltages measured at the left leg and the left wrist, for example, as expressed in equation 5:

$$V_{III} = V_F - V_L \quad (5)$$

$$-V_{III} = V_L - V_F \quad (6)$$

Equations 5 and 6 thus can be inversions of one another. This can mean that depending on which electrodes is the positive electrode and which electrode is the negative electrode, the results can be inverted with respect to one another.

Figure 2:
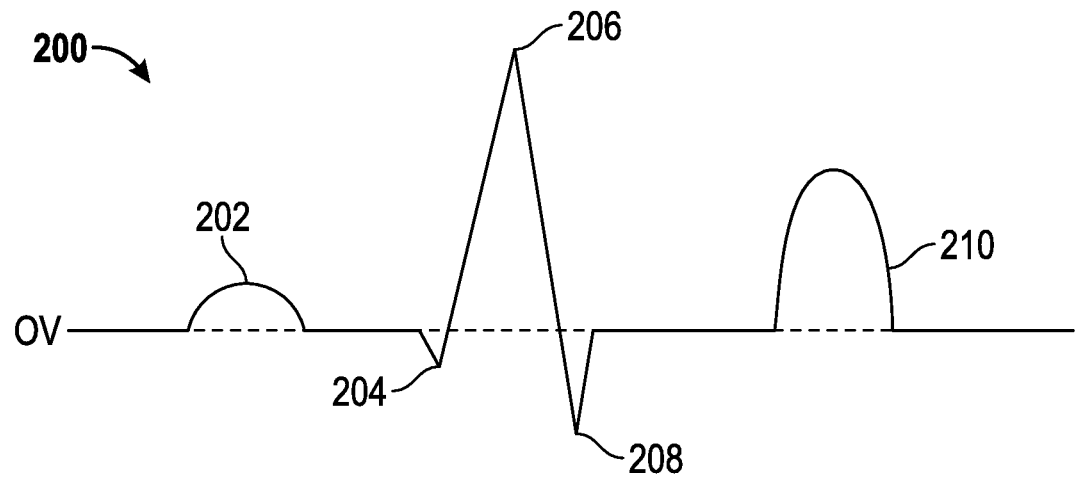
FIG. 2 illustrates an exemplary electrocardiographic measurement according to examples of the disclosure.

FIG. 2 illustrates an exemplary electrocardiographic measurement according to examples of the disclosure. In this example, the measurement can be made when the electrodes are placed in the Lead I configuration, with the positive electrode on the left wrist and the negative electrode on the right wrist. The potential difference between the two electrodes can vary based on electrical signals being produced by the heart as part of its normal function. Measurement 200 can represent the varying potential between the two electrodes over one cycle of a heartbeat. For instance, initially at 202, the potential difference can rise and then fall for a brief duration. This initial rise and fall can correspond to atrial depolarization of the heart muscle and is known in the art as a P-wave. At 204, the potential between the two electrodes can fall for a brief period of time. The fall can correspond to septal depolarization and is known in the art as a Q-wave. At 206, the potential difference can have a sharp rise. The rise can correspond to apical depolarization (i.e., when the majority of the ventricle tissue depolarizes) and is known in the art as an R-wave. At 208, the potential difference can fall. The fall can correspond to left ventricular depolarization and is known in the art as an S-wave. Finally at 210, the potential difference can rise and fall for a brief duration. This final rise and fall can correspond to ventricular repolarization and is known in the art as a T-wave.

Figure 3A:
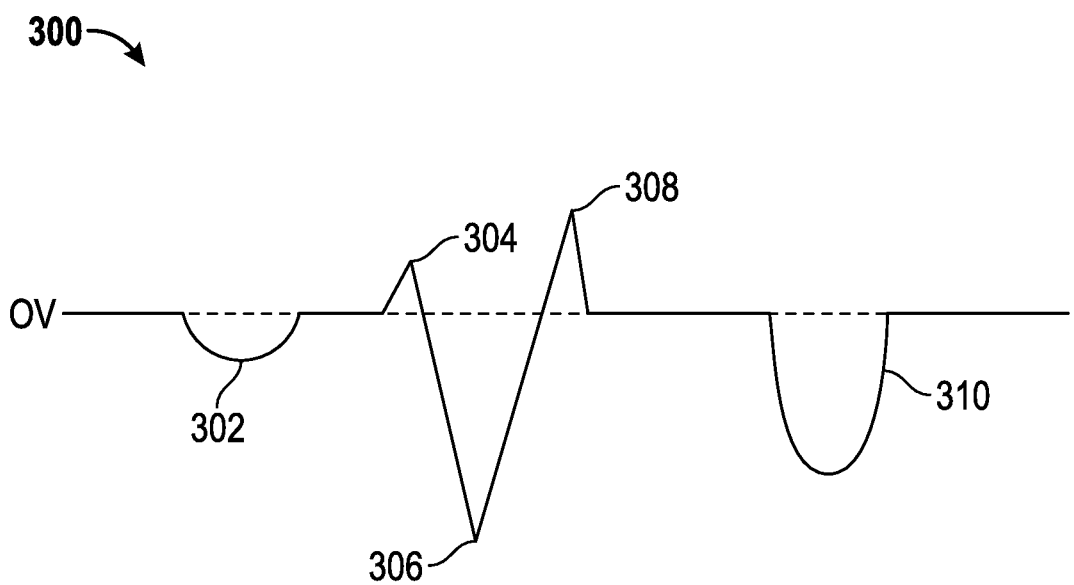
FIG. 3a-3c illustrate exemplary electrocardiographic measurements resulting from lead inversion according to examples of the disclosure.
Figure 3B:
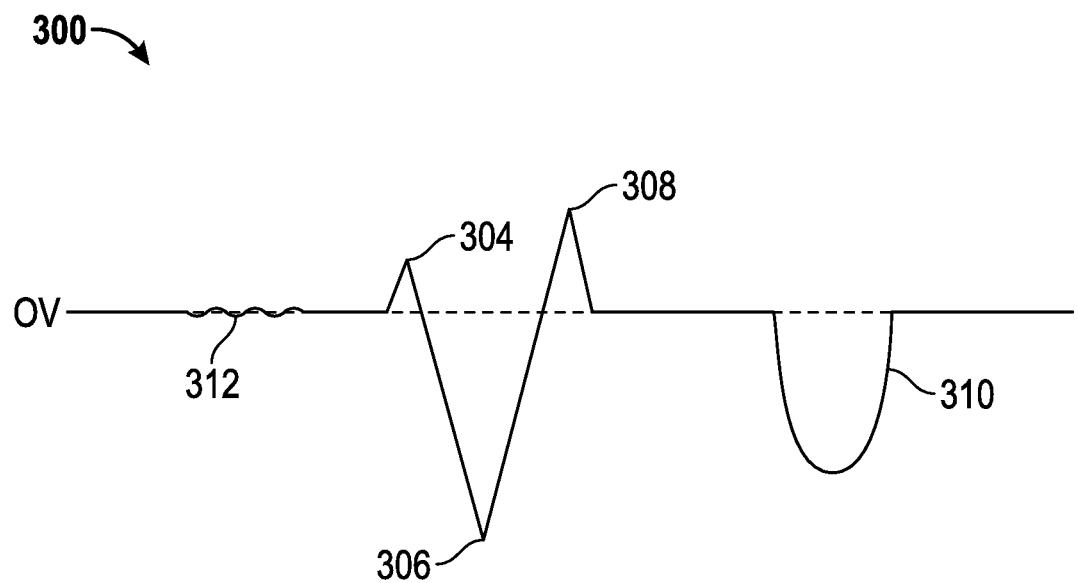
Figure 3C:
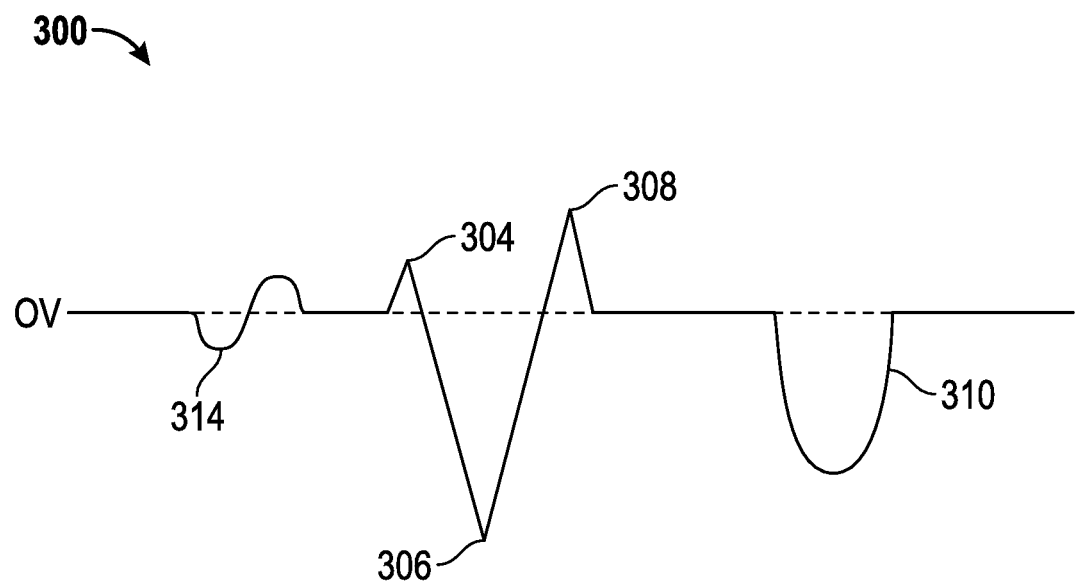

FIGS. 3a-3c illustrate exemplary electrocardiographic measurements resulting from lead inversion according to examples of the disclosure. In these examples, the measurement can be made when the electrodes are placed in the Lead I configuration, with the positive electrode on the right wrist and the negative electrode on the left wrist. By placing the electrodes in this configuration, the resulting electrocardiographic measurement can be inverted relative to a measurement taken with the electrodes oriented as in the example of FIG. 2. Referring to FIG. 3a, measurement 300 can represent the varying potential between the electrodes over one cycle of a heartbeat. Since the electrodes are reversed in reference to the example of FIG. 2, the electrocardiographic measurement will be inverted with respect to the measurement illustrated in FIG. 2. As an example, the P-wave 202 of FIG. 2 can appear as a decrease in potential difference illustrated at 302 in FIG. 3a. The P-wave can also appear to be insignificant (i.e., have a small amplitude) as shown at 312 of FIG. 3b. In another example, the P-wave can appear to be bi-phasic as illustrated at 314 of FIG. 3c. The R-wave 206 of FIG. 2 can appear as a sharp decrease in potential difference, illustrated at 306 in FIG. 3. Similar results can occur for the Q, S, and T waves.

Lead inversion can create identification issues in the processing of electrocardiographic measurements. For instance, referring to FIG. 2, when the electrocardiographic measurement is processed to identify the P, Q, R, S and T waves, an example algorithm can search for the first sharp increase in potential such as what occurs at 206, and classify that sharp increase as the R-wave that can correspond to apical depolarization and left ventricular depolarization. In the example of FIG. 2, this classification would most likely be correct. However, using this same principle to search for the R-wave in the example of FIG. 3a, the algorithm may attribute the R-wave to either the potential increase which occurs at 304, or the potential increase that occurs at 308. As discussed above, however; the potential increases at 304 and 306 can correspond to the Q-wave and S-wave of the heart cycle and only appear as potential increases due to the fact that the positions of the positive electrode and the negative electrode have been reversed.

Because of this fact, medical practitioners often have to take care as to the placement of the positive electrode and the negative electrode to ensure accurate processing of an electrocardiographic measurement. However, in some contexts, ensuring that the leads are placed in the correct position in order to prevent lead inversion errors may not be feasible.

Figure 4:
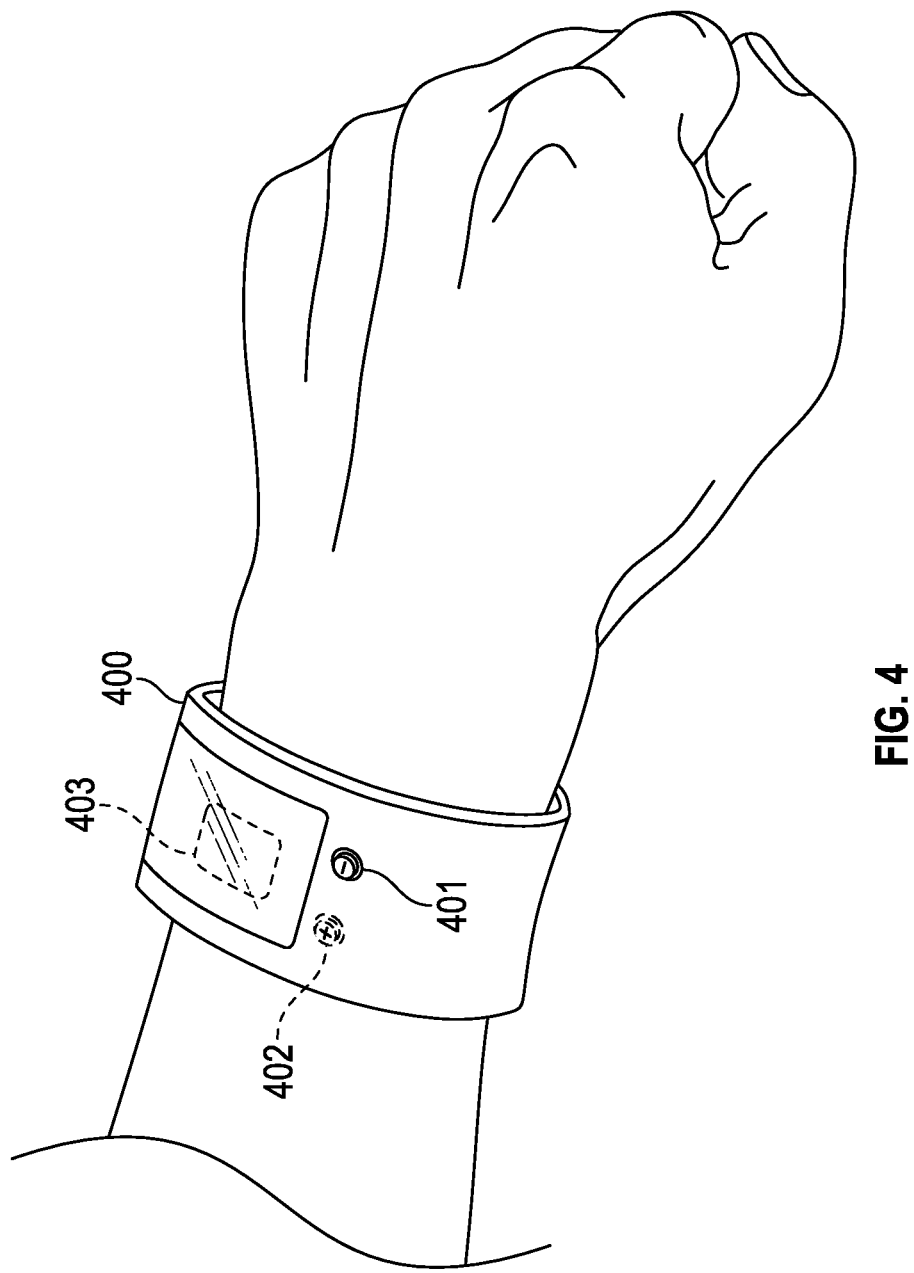
FIG. 4 illustrates an exemplary wearable device capable of recording an electrocardiographic measurement according to examples of the disclosures.

FIG. 4 illustrates an exemplary wearable device capable of recording an electrocardiographic measurement according to examples of the disclosures. Wearable device 400 can be worn by a user on the wrist (as pictured) or the ankle/leg of the user, or any other part of the human body. Wearable device 400 can be configured to have three electrocardiographic electrodes 401, 402, and 403. In the example of FIG. 4, electrode 402 can act as the positive electrode for the purpose of measuring the potential difference from electrode 401, which can act as the negative electrode. The potentials at electrode 401 and 402 can be measured with respect to the ground electrode 403. Also, in the example of FIG. 4, the positive electrode 402 and the ground electrode 403 can be positioned such that they are in direct contact with the wrist (i.e., on the underside of the wearable device 400), while electrode 401 can be positioned such that it is not in contact with any portion of the user's body as illustrated. In order to take an electrocardiographic measurement, the user can place a part of his or her body, such as a finger, on the open electrode (i.e., electrode 401) that is not already in contact with the user's body. For instance, the user can place his or her finger on electrode 401, or can place electrode 401 in contact with either ankle. Once electrode 401 has made contact with a portion of the user's body, an electrocardiographic measurement that measures the potential difference between the portion of the body in contact with electrode 402 and the portion of the body in contact with electrode 401 can be acquired.

Figure 5:
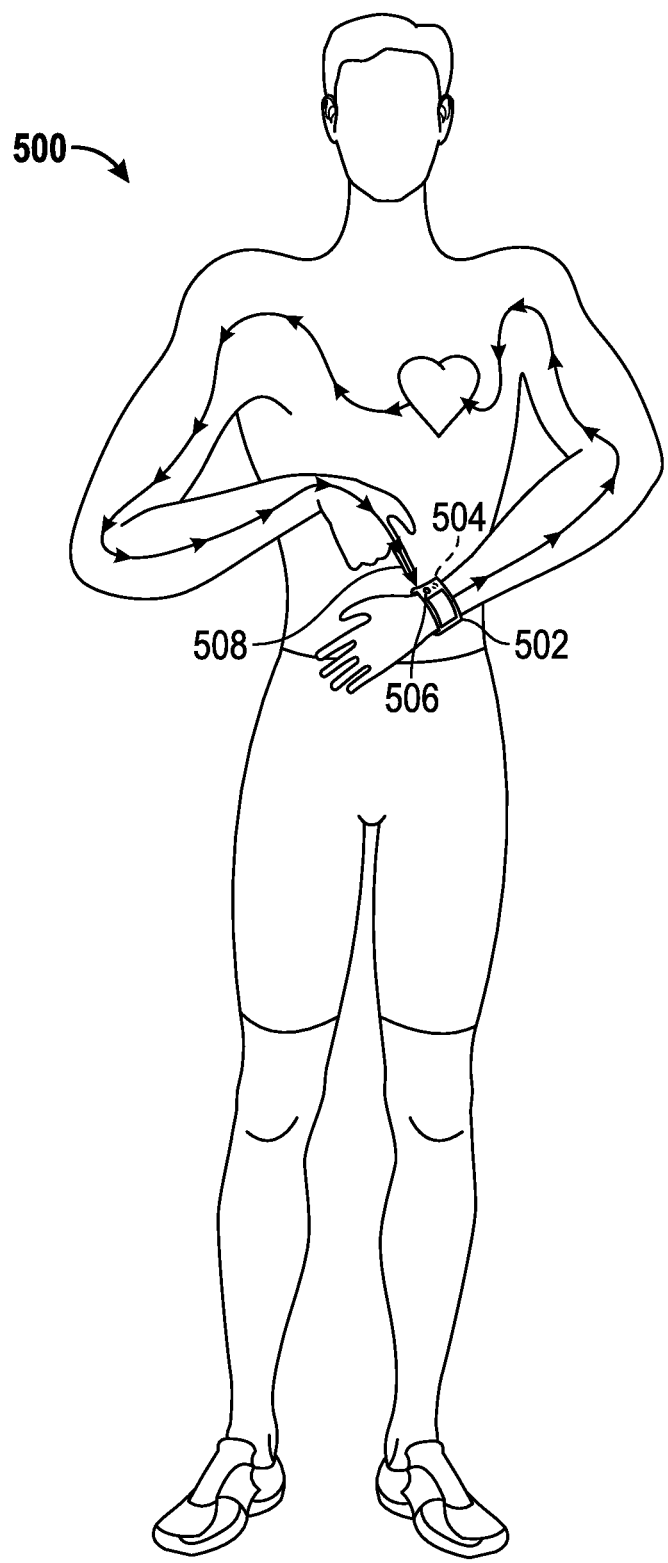
FIG. 5 illustrates an exemplary placement of a wearable device on the user according to examples of the disclosure.

FIG. 5 illustrates an exemplary placement of a wearable device on the user according to examples of the disclosure. In the example of FIG. 5, the wearable device 502 is shown as being worn on the left wrist of the user 500. In this placement, the positive electrode 504 can be on the underside of the wearable device 502, with the positive electrode touching the left wrist of the user. In order to record an electrocardiographic measurement, the user 500 can place one of the right hand fingers 508 on the negative electrode 506. The device can measure the potential difference between the left wrist of the user and one of the right hand fingers of the user. An electrocardiographic measurement obtained in this manner can correspond to the Lead I configuration illustrated in FIG. 1 at side 108 of Einthoven's triangle. Since the positive electrode 504 is placed at the left wrist, while the negative electrode 506 is being touched by a right hand finger 508, equation 1 above can be used to characterize the electrocardiographic measurement.

Figure 6:
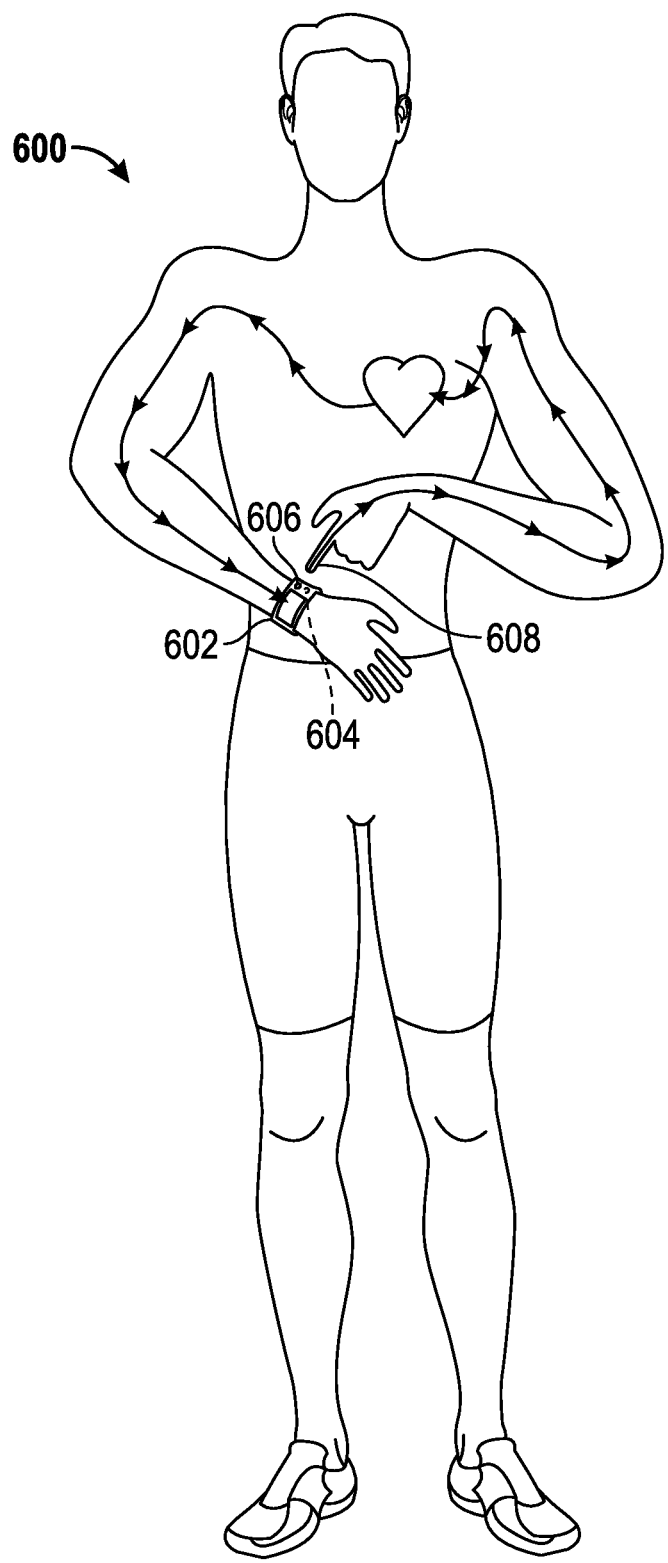
FIG. 6 illustrates another exemplary placement of a wearable device on the user according to examples of the disclosure.

FIG. 6 illustrates another exemplary placement of a wearable device on the user according to examples of the disclosure. In the example of FIG. 6, the wearable device 502 is shown as being worn on the right wrist of the user 600. In this placement, the positive electrode 604 can be on the underside of the wearable device 602 with the electrode touching the right wrist of the user. In order to record an electrocardiographic measurement, the user 600 can place one of the left hand fingers 608 on the negative electrode 606. The device can measure the potential difference between the right wrist of the user and the left hand finger of the user. An electrocardiographic measurement obtained in this manner can correspond to an inverted Lead I configuration illustrated in FIG. 1 at side 108 of Einthoven's triangle. Since the positive electrode 604 is placed at the right wrist while the negative electrode 606 is being touched by the left hand finger 608, equation 2 above can be used to characterize the electrocardiographic measurement.

As discussed above, equations 1 and 2 can be inversions of one another. This can mean that if the user wears the device on their left wrist, the electrocardiographic measurement can be taken with the P, Q, R, S and T waves detected correctly. However, if the user wears the device on the right wrist, the measurement may be inverted and the waves may not be classified correctly, leading to a deficient measurement. In order to maintain flexibility as to where on the body the user can wear the device, a method of detecting the wearing limb and correcting for lead inversion can be employed in order to correct electrocardiographic measurements that have been inverted as discussed above.

Figure 7:
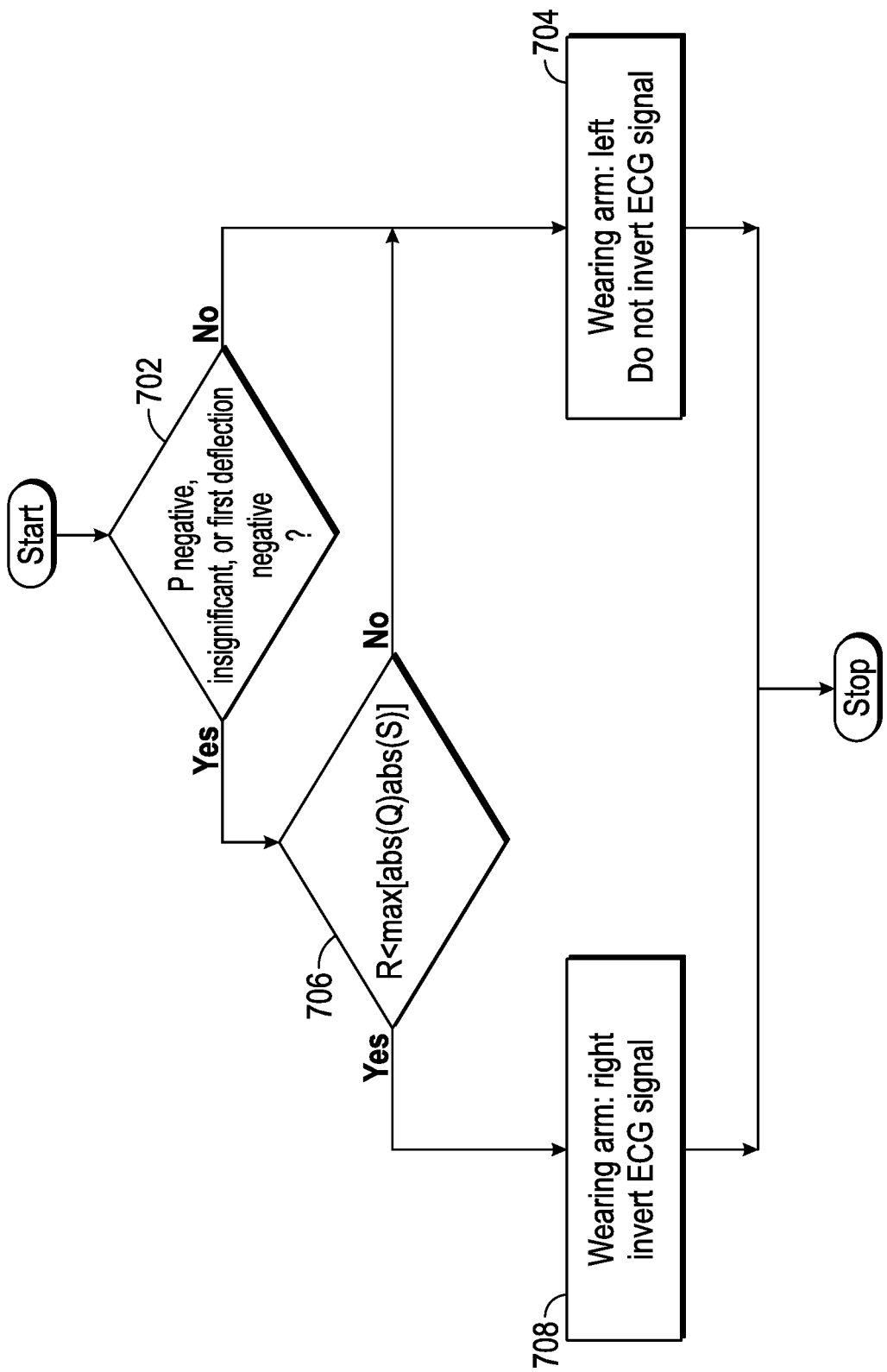
FIG. 7 illustrates an exemplary method for detecting lead inversion and correcting the acquired electrocardiographic measurement according to examples of the disclosure.

FIG. 7 illustrates an exemplary method for detecting lead inversion and correcting the acquired electrocardiographic measurement according to examples of the disclosure. In addition to detecting lead inversion, the method depicted in FIG. 7 can also be used to detect the wearing limb of the device. Such knowledge may be useful in other biomedical applications such as diagnosing peripheral arterial occlusion disease, peripheral venous disease, and blood pressure as examples. The example of FIG. 7 is illustrated using the right and left wrists as an example, but could apply to other portions of the body. At step 702 the P-wave (as classified by the electrocardiographic processing method described above) is analyzed. If the amplitude of the P-wave is negative (as depicted at 302 in FIG. 3*a*) or insignificant (as depicted at 312 in FIG. 3*b*), or biphasic and the first deflection is negative (as depicted at 314 in FIG. 3*c*), the method can move on to step 706. As illustrated in FIG. 3, which illustrates an electrocardiographic measurement that has been inverted due to lead inversion, the P-wave 302 can have a negative amplitude. In contrast, as illustrated in FIG. 2 (which illustrates a non-inverted electrocardiographic measurement), the P-wave can have a positive amplitude. If a positive P-wave is detected (in other words, the P-wave amplitude is above a pre-determined threshold), then the method can move to step 704 and a determination can be made that the device is being worn on the left wrist. Detecting a negative, or insignificant, or biphasic P-wave with the first deflection negative may not in and of itself be determinative of an inverted electrocardiographic measurement. This can be due to various cardiovascular pathologies wherein a certain portion of the human population can have negative or insignificant P-waves as part of their normal cardiac function. Therefore, if a negative or insignificant or a biphasic P-wave with first deflection negative is detected, the method can move on to step 706.

At step 706, the magnitude of the R-wave can be compared with the magnitude of the Q-wave and the S-wave. If the magnitude of the R-wave is less than the maximum among the magnitudes of the Q-wave and S-wave, the method can determine that the leads have been inverted. As illustrated in FIGS. 3*a*-3*c* and as discussed above, when lead inversion occurs, a processing algorithm can inaccurately identify the Q, R, and S waves. As discussed above in reference to FIG. 3, the algorithm may characterize the potential change at 304 as the R-wave and the potential change at 306 as the S-wave. If such a misclassification were to occur, the magnitude of the R-wave will be less than the magnitude of the misclassified S-wave. Under such a scenario, the method can determine that the leads have been inverted. Alternatively, in the measurement of FIG. 3, the potential change at 306 can be misclassified as the Q-wave, while the potential change at 308 can be misclassified as the R-wave. In such a scenario, the magnitude of the R-wave will be less than the magnitude of the Q-wave, and the method can determine that lead inversion has occurred and that the device is being worn on the right wrist at 708. If the magnitude of the R-wave is greater than the maximum of the magnitudes of the Q-wave and the S-wave then the method can move to 704 and can determine that the device is being worn on the left wrist and that no lead inversion has occurred.

The method illustrated in FIG. 7 can distinguish an inverted electrocardiographic measurement from a non-inverted electrocardiogram measurement. It may not, however, be able to determine which limb of the user the device is being worn. It also may not be able to determine which limb of the user is touching the negative electrode in order to acquire the measurement. In a scenario in which the wearable device is restricted to being worn on the wrist, the method described in FIG. 7 may be adequate since it is known a priori that the device is being worn on the wrist, and based on the determination of whether electrocardiographic reading is inverted or not, the wrist the device is being worn on (left v. right) can also be known. Knowing the wrist or limb on which the device is worn may also be useful for other biological measurements performed by the device, for example blood pressure, temperature or pulse transition time. However in a scenario in which the wearable device is not restricted to being worn on a particular limb, the method of FIG. 7 may be prone to errors since the electrocardiographic measurement shape and features depends on which pair of limbs the measurement is being taken from.

Figure 8:
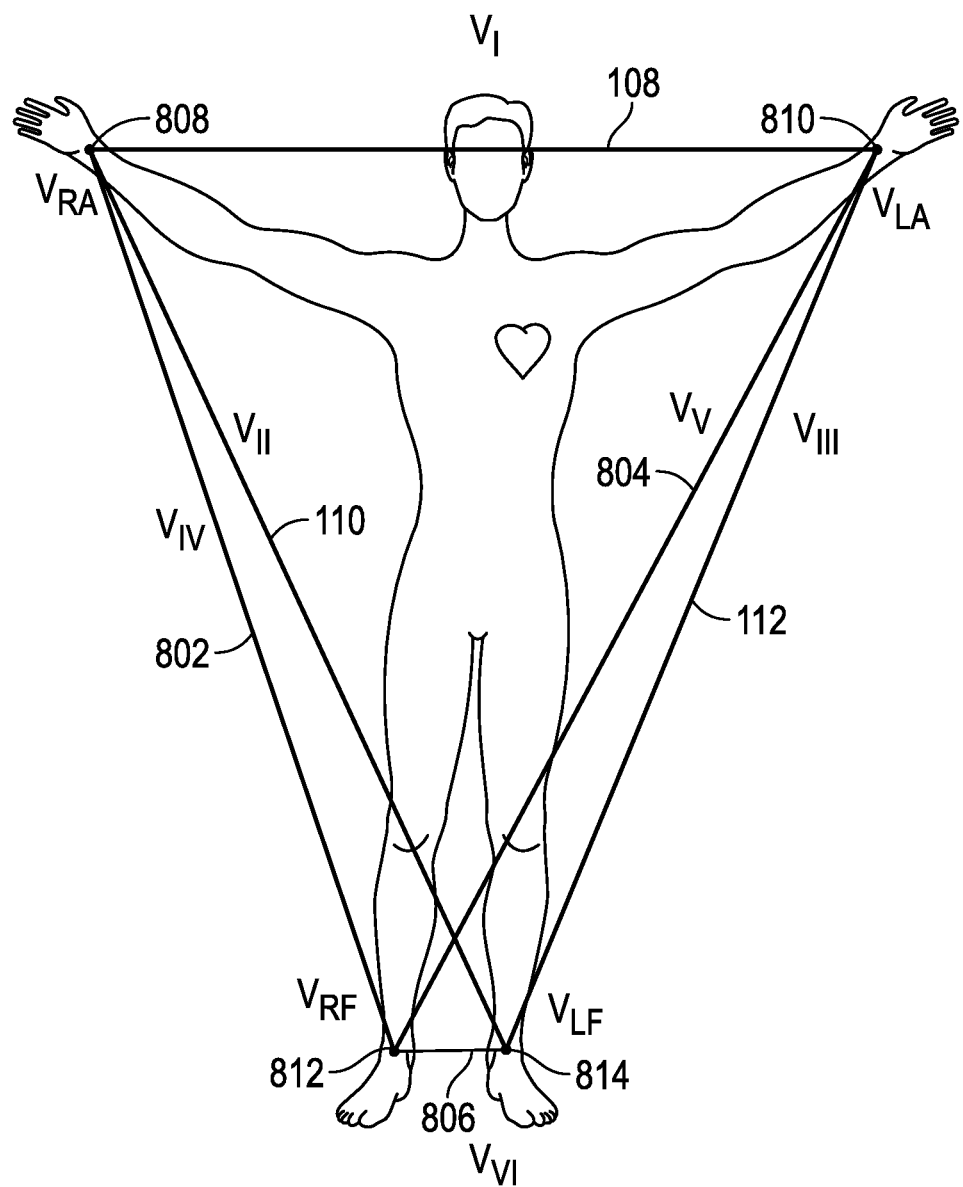
FIG. 8 illustrates additional electrocardiographic lead configurations according to examples of the disclosure.

FIG. 8 illustrates additional electrocardiographic lead configurations according to examples of the disclosure. If the wearable device could be worn on any wrist or any leg of the user's body, then non-standard electrocardiographic leads can be defined between the right leg and other limbs, thereby expanding Einthoven's triangle illustrated in FIG. 1 and explained above. As illustrated, Leads I, II, and III (108, 110, and 112) from FIG. 1 and discussed above can represent different scenarios in which the device is worn on either the left wrist, right wrist, or the left ankle. If the device can also be worn on the right ankle, then a second triangle can be formed with sides 802, 804 and 108.

Side 802 can represent a non-standard Lead IV configuration and can represent the potential difference between the right ankle and the right wrist. The potential difference could be measured, for instance, if the user was to wear the device on their right ankle and touch with one of the right hand fingers the negative electrode. This potential difference can be expressed as the difference between the voltages measured at the right ankle and the right wrist, for example, as expressed in equation 7:

$$V_{IV} = V_{RF} - V_{RA} \tag{7}$$

The potential difference between the right wrist and the left ankle can also be expressed as:

$$-V_{IV} = V_{RA} - V_{RF} \tag{8}$$

if the device is worn on the right wrist and the right ankle is touching the negative electrode of the device. Equations 7 and 8 thus can be inversions of one another. This can mean that depending on which limb is wearing the device (right wrist or right leg) or which electrode is the positive electrode and which electrode is the negative electrode, the results can be inverted with respect to one another.

The non-standard Lead V configuration (side 804) can measure the potential difference between the right ankle 812 and the left wrist 810. This potential difference can be expressed as the difference between the voltages measured at the right ankle and the left wrist, for example, as expressed in equation 9:

$$V_V = V_{RF} - V_{LA} \tag{9}$$

The potential difference between the left wrist and the right ankle can also be expressed as:

$$-V_V = V_{LA} - V_{RF} \tag{10}$$

Equations 9 and 10 thus can be inversions of one another. This can mean that depending on which electrode is the positive electrode and which electrode is the negative electrode, the results can be inverted with respect to one another.

The non-standard Lead VI configuration can measure the potential difference between the left ankle and the right ankle, for example, as expressed in equation 11:

$$V_{VI} = V_{LF} - V_{RF} \tag{11}$$

The potential difference between the right ankle and the left ankle can also be expressed as:

$$-V_{VI} = V_{RF} - V_{LF} \tag{12}$$

Equations 11 and 12 thus can be inversions of one another. This can mean that depending on which electrode is the positive electrode and which electrode is the negative electrode, the results can be inverted with respect to one another. The six Lead configurations as described for the purpose of this disclosure can be summarized below in Table 1.

| Lead | Positive Limb (wearing limb) | Negative Limb | Representative Equation |
|---|---|---|---|
| I | Left wrist | Right wrist | $V_I = V_{LA} - V_{RA}$ |
| II | Left ankle | Right wrist | $V_{II} = V_{LF} - V_{RA}$ |
| III | Left ankle | Left wrist | $V_{III} = V_{LF} - V_{LA}$ |
| IV | Right ankle | Right wrist | $V_{IV} = V_{RF} - V_{RA}$ |
| V | Right ankle | Left wrist | $V_V = V_{RF} - V_{LA}$ |
| VI | Left ankle | Right ankle | $V_{VI} = V_{LF} - V_{RF}$ |

Based on the mathematical relationships expressed above in Table 1, it may not be necessary to record all six lead configurations in order to ascertain the potential differences expressed in the equations pertaining to each lead. For examples Leads, I, II and V can be measured as described above. With these three measurements, and using Kirchhoff's rule, the potential differences for the Lead III, IV, and VI configurations can be derived using the equations below:

$$V_{III} = V_{II} - V_I \tag{13}$$

$$V_{IV} = V_I + V_V \tag{14}$$

$$V_{VI} = V_{II} - V_I - V_V \tag{15}$$

As an example, the potential difference that can be obtained in the Lead III configuration can be derived by obtaining measurements in the Lead II configuration and the Lead I configuration and then subtracting the results from each other. Equations 13, 14 and 15 illustrate that in order to measure the potential difference in all six of the lead configurations discussed above; one may only have to measure the potential difference in three of the lead configurations and can then derive the remaining potential differences for the remaining lead configurations.

Figure 9:
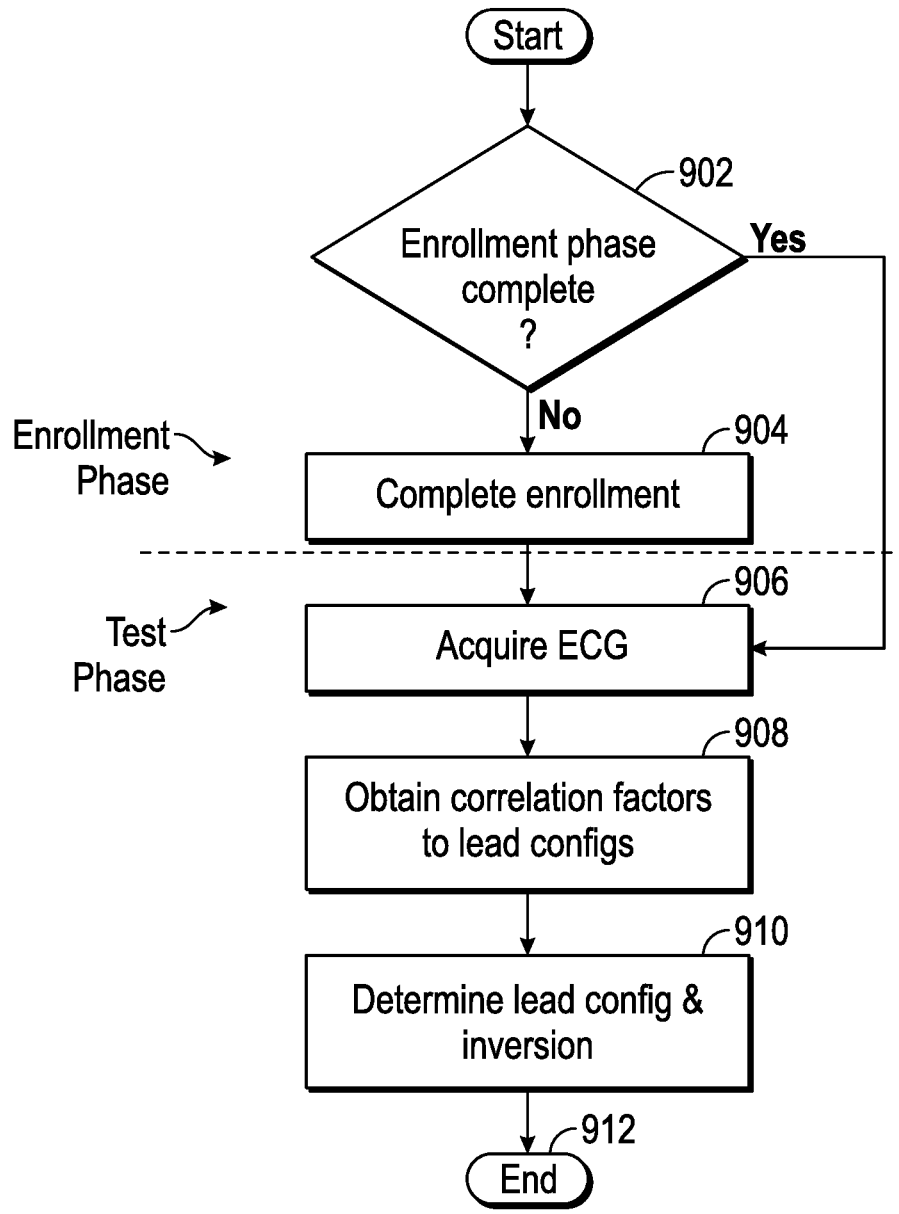
FIG. 9 illustrates another exemplary method for detecting lead inversion of an electrocardiographic measurement according to examples of the disclosure.

FIG. 9 illustrates another exemplary method for detecting and correcting for lead inversion of an electrocardiographic measurement according to examples of the disclosure. The method illustrated in FIG. 9 can contain two phases, an enrollment phase and a test phase. At step 902, the device can determine if the enrollment phase (described below) has been completed. If it is determined that the enrollment phase has been completed, the method can move to the beginning of the test phase which can begin at step 906. If the user has not been enrolled, then the method can move to step 904 in order to enroll the user.

Enrolling the user can include taking a series of electrocardiographic measurements in various lead configurations when the user first uses the wearable device, in order to create a database for the device to compare future acquired electrocardiographic measurements against the measurements stored in the database. The enrollment phase may only need to be performed once per user of the device in order to create the database that future acquired measurements can be compared against.

Figure 10:
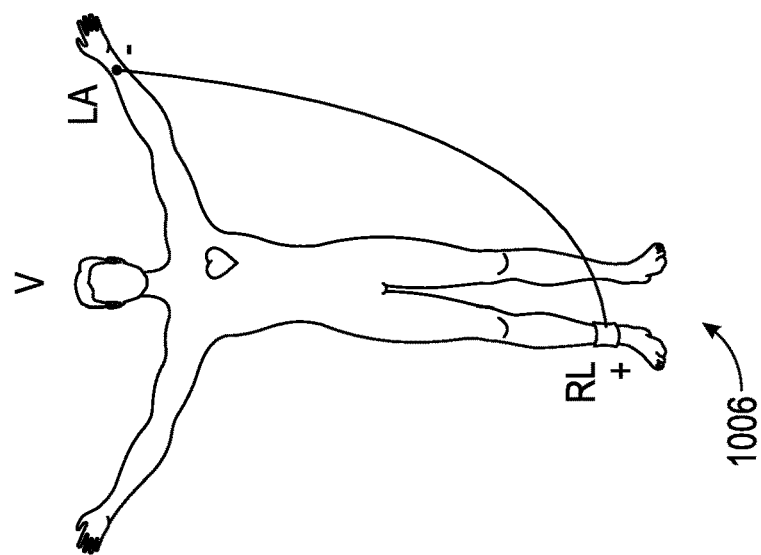
FIG. 10 illustrates various enrollment phase lead configurations according to examples of the disclosure.
Figure 10:
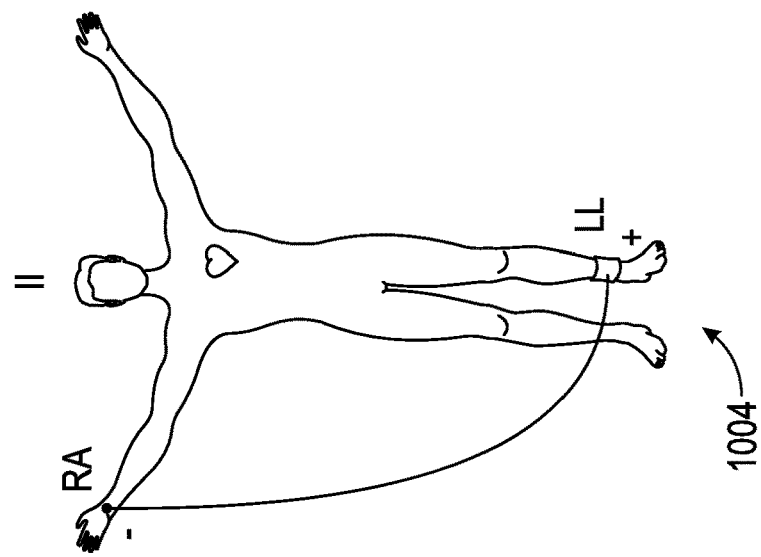
Figure 10:
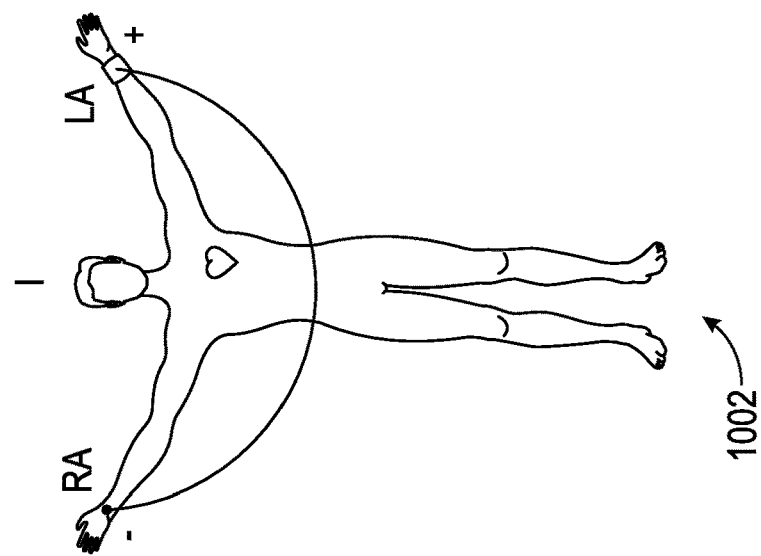

FIG. 10 illustrates various enrollment phase lead configurations according to examples of the disclosure. As illustrated at 1002, as part of the enrollment phase, the device can be worn in the Lead I configuration with the device on the left wrist and the negative electrode making contact with a finger of the right wrist. After the measurement has been obtained in the Lead I configuration, the device can prompt the user to wear the device in the Lead II configuration with the device being worn on the left leg and a finger of the right arm making contact with the negative electrode of the device, as illustrated at 1004. After the measurement has been obtained in the Lead II configuration, the device can prompt the user to wear the device in the Lead V configuration with the device being worn on the right leg and one of the fingers of the left arm making contact with the negative electrode, as illustrated at 1006.

With these three measurements stored in the device, the measurements for Lead III, IV, and VI can be derived as described above. Therefore at the end of the enrollment phase, the device can have stored six different measurements, one for each lead. A processor in the device can then calculate the positions of the QRS complexes (or R waves) and can compute an average template for each of the 6 leads by overlapping and averaging the recorded beats in synchrony with the R waves. A time scaling can be applied to normalize each template lead to a given heart rate such as 60 bpm (beats per minute) using the same principles used in QT interval correction known in the art. A normalization in amplitude can also be applied. The 6 templates are stored for use in the subsequent test (detection) phases.

Returning to the method illustrated at FIG. 9, once the enrollment phase has been completed, the method can then move to step 906 where an electrocardiographic measurement can be acquired. Acquiring the electrocardiographic measurement can include calculating the position of the QRS complexes (or R waves) and computing an average template for the recorded measurement by overlapping the recorded beats in synchrony with the R waves. As in the enrollment phase, a time scaling can be applied to normalize the template for fluctuations in heart rate and amplitude normalization can also be performed.

Once the electrocardiographic measurement has been acquired at step 906, the method can move to step 908. At step 908, the acquired electrocardiogram reading can be compared to the six template readings acquired during the enrollment phase. The comparison can include computing the cross-correlations between the acquired and normalized measurement acquired at step 906 and each of the six stored templates acquired in the enrollment phase. In one example, a cross-correlation factor ranging from −1 to +1 can be computed for each of the six lead templates. The cross-correlation factor can thus represent a measure of the correlation between the acquired measurement and each of the six lead templates. A correlation factor of −1 can mean the two signals are inversely correlated with each other (i.e., one is the inversion of the other), while a correlation factor close to +1 can mean that the two signals are nearly identical.

Figure 11:
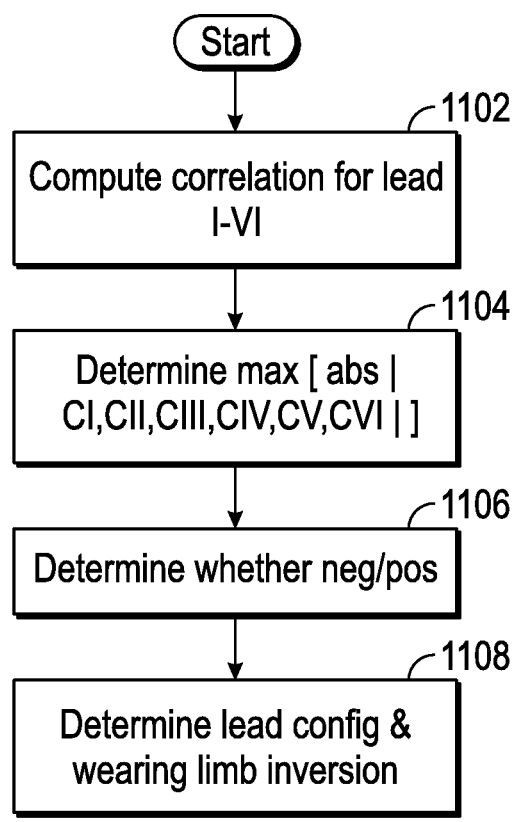
FIG. 11 illustrates an exemplary method for determining lead configuration and inversion according to examples of the disclosure.

FIG. 11 illustrates an exemplary method for determining lead configuration and inversion according to examples. The method illustrated in FIG. 11 can correspond to step 908 and 910 of FIG. 9. At step 1102, correlation factors between the acquired ECG signal and the six templates acquired during the enrollment phase can be computed. At step 1104 the maximum of the absolute values (max abs) of the six computed correlation factors can be calculated. Once the max abs correlation factor is determined, the method can then move to step 1106 where a determination can be made as to whether the max abs correlation factor was originally positive or negative. At step 1108, the method can determine that the device is in the Lead configuration that produced the max abs correlation factor, and based on the polarity of the correlation factor can determine if the leads have been inverted. As an example, if the acquired data produces the following set of correlation factors corresponding to the Lead I-VI templates:

[+0.2, −0.5, −0.6, −0.9, +0.3, +0.1]

then the max abs of the set of correlations factors can be +0.9 which corresponds to the Lead IV template (i.e., the fourth element of the matrix above). Thus, the method can determine that the device is in the Lead IV configuration. Since the Lead IV template produced a correlation factor of −0.9, the device can determine that the leads are inverted. Referring to Table I, an inverted Lead IV configuration can mean that the device is being worn on the right wrist and the right ankle is touching the negative electrode. If the device determines that the leads are inverted, it can process the acquired data to correct for the inversion.

One way the device can correct for a detected inversion is to "flip" the data around the x-axis. In one example, lead inversion can mean that the data is flipped about the x-axis; in other words, when data is inverted, the negative values appear as positive and the positive values appear as negative. Thus, correction can simply mean multiplying a measured result by −1 in order to correct for the inversion.

Therefore, according to the above, some examples of the disclosure are directed to a device capable of measuring electrocardiographic signals, the device comprising: a first electrode configured to come into contact with a first portion of the user's body and configured to measure an electrical potential at the first portion of the user's body; a second electrode configured to come into contact with a second portion of the user's body and configured to measure an electrical potential at the second portion of the user's body; and a processor capable of: measuring a potential difference between the first electrode and the second electrode; determining whether the first electrode and second electrode have been inverted based on the measured potential difference between the first electrode and the second electrode, wherein determining whether the first electrode and second electrode have been inverted includes identifying a P-wave, an R-wave, a Q-wave, and an S-wave from the measured potential difference; and compensating the measured potential difference if the first and second electrodes are determined to be inverted. Additionally or alternatively to one or more of the examples disclosed above, in some examples, determining whether the first electrode and the second electrode have been inverted further includes determining if the P-wave exhibits a characteristic indicative of inversion of the first and second electrodes. Additionally or alternatively to one or more of the examples disclosed above, in some examples, determining whether the first electrode and the second electrode have been inverted further includes comparing an amplitude of the R-wave to the maximum of the absolute values of the amplitudes of the Q-wave and the S-wave, if the amplitude of the P-wave is lower than a pre-determined threshold. Additionally or alternatively to one or more of the examples disclosed above, in some examples, the processor is further capable of determining a location on the user's body of the first electrode and a location on the user's body of the second electrode based on the determination of whether the first electrode and the second electrode have been inverted.

Some examples of the disclosure are directed to a method of detecting and correcting lead inversion in an electrocardiographic measurement, the method comprising: measuring a potential difference between a first electrode and a second electrode, the first electrode and second electrode being in contact with a first portion and a second portion respectively of a user's body; determining whether the first electrode and second electrode have been inverted based on the measured potential difference between the first electrode and the second electrode, wherein determining whether the first electrode and second electrode have been inverted includes identifying a P-wave, an R-wave, a Q-wave, and an S-wave from the measured potential difference; and compensating the measured potential difference if the first and second electrodes are determined to be inverted. Additionally or alternatively to one or more of the examples disclosed above, in some examples, determining whether the first electrode and the second electrode have been inverted further includes determining if the P-wave exhibits a characteristic indicative of inversion of the first and second electrodes. Additionally or alternatively to one or more of the examples disclosed above, in some examples, determining whether the first electrode and the second electrode have been inverted further includes comparing an amplitude of the R-wave to the maximum of the absolute values of the amplitudes of the Q-wave and the S-wave, if the amplitude of the P-wave is lower than a pre-determined threshold. Additionally or alternatively to one or more of the examples disclosed above, in some examples, the method further comprising determining a location on the user's body of the first electrode and a location on the user's body of the second electrode based on the determination of whether the first electrode and the second electrode have been inverted.

Some examples of the disclosure are directed to a non-transitory computer readable storage medium having stored thereon a set of instructions for detecting and correcting lead inversion in an electrocardiographic measurement, that when executed by a processor causes the processor to: measure a potential difference between a first electrode and a second electrode, the first electrode and second electrode being in contact with a first portion and a second portion respectively of a user's body; determine whether the first electrode and second electrode have been inverted based on the measured potential difference between the first electrode and the second electrode, wherein determining whether the first electrode and second electrode have been inverted includes identifying a P-wave, an R-wave, a Q-wave, and an S-wave from the measured potential difference; and compensate the measured potential difference if the first and second electrodes are determined to be inverted. Additionally or alternatively to one or more of the examples disclosed above, in some examples, determining whether the first electrode and the second electrode have been inverted further includes determining if the P-wave exhibits a characteristic indicative of inversion of the first and second electrodes. Additionally or alternatively to one or more of the examples disclosed above, in some examples, determining whether the first electrode and the second electrode have been inverted further includes comparing an amplitude of the R-wave to the maximum of the absolute values of the amplitudes of the Q-wave and the S-wave, if the amplitude of the P-wave is lower than a pre-determined threshold. Additionally or alternatively to one or more of the examples disclosed above, in some examples, the method further comprising determining a location on the user's body of the first electrode and a location on the user's body of the second electrode based on the determination of whether the first electrode and the second electrode have been inverted.

Some examples of the disclosure are directed to a device capable of measuring electrocardiographic signals, the device comprising: a first electrode configured to come into contact with a first portion of the user's body and configured to measure an electrical potential at the first portion of the user's body; a second electrode configured to come into contact with a second portion of the user's body and configured to measure an electrical potential at the second portion of the user's body; and a processor capable of: measuring a potential difference between the first electrode and the second electrode; determining whether the first electrode and the second electrode have been inverted based on the measured potential difference between the first electrode and the second electrode, wherein determining whether the first electrode and the second electrode have been inverted includes comparing the measured potential difference to a plurality of electrocardiographic measurements stored in a memory of the device. Additionally or alternatively to one or more of the examples disclosed above, in some examples, the plurality of electrocardiographic measurements are obtained in an enrollment phase of the device, wherein during the enrollment phase the first electrode and the second electrode are placed in a plurality of known locations on the user's body to generate the plurality of electrocardiographic measurements. Additionally or alternatively to one or more of the examples disclosed above, in some examples, comparing the measured potential difference to a plurality of electrocardiographic measurements stored in a memory of the device includes generating a cross-correlation factor between the measured potential difference and each of the electrocardiographic measurements stored in the memory of the device. Additionally or alternatively to one or more of the examples disclosed above, in some examples, the processor is further capable of determining a location on the user's body of the first electrode and a location on the user's body of the second electrode based on the plurality of correlation factors generated.

Some examples of the disclosure are directed to a method of detecting and correcting lead inversion in an electrocardiographic measurement, the method comprising: measuring a potential difference between a first electrode and a second electrode, the first electrode and second electrode being in contact with a first portion and a second portion respectively of a user's body; determining whether the first electrode and the second electrode have been inverted based on the measured potential difference between the first electrode and the second electrode, wherein determining whether the first electrode and the second electrode have been inverted includes comparing the measured potential difference to a plurality of stored electrocardiographic measurements; compensating the measured potential difference if the first and second electrodes are determined to be inverted. Additionally or alternatively to one or more of the examples disclosed above, in some examples, the plurality of electrocardiographic measurements are obtained by placing the first electrode and the second electrode in a plurality of known locations on the user's body to generate the plurality of stored electrocardiographic measurements. Additionally or alternatively to one or more of the examples disclosed above, in some examples, comparing the measured potential difference to a plurality of electrocardiographic measurements includes generating a cross-correlation factor between the measured potential difference and each of the stored electrocardiographic measurements of the plurality of stored electrocardiographic measurements. Additionally or alternatively to one or more of the examples disclosed above, in some examples, the method further comprises determining a location on the user's body of the first electrode and a location on the user's body of the second electrode based on the plurality of correlation factors generated.

Some examples of the disclosure are directed to a non-transitory computer readable storage medium having stored thereon a set of instructions for detecting and correcting lead inversion in an electrocardiographic measurement, that when executed by a processor causes the processor to: measure a potential difference between a first electrode and a second electrode, the first electrode and second electrode being in contact with a first portion and a second portion respectively of a user's body; determine whether the first electrode and the second electrode have been inverted based on the measured potential difference between the first electrode and the second electrode, wherein determining whether the first electrode and the second electrode have been inverted includes comparing the measured potential difference to a plurality of electrocardiographic measurements stored in a memory; compensate the measured potential difference if the first and second electrodes are determined to be inverted. Additionally or alternatively to one or more of the examples disclosed above, in some examples, the plurality of electrocardiographic measurements are obtained by placing the first electrode and the second electrode in a plurality of known locations on the user's body to generate the plurality of stored electrocardiographic measurements. Additionally or alternatively to one or more of the examples disclosed above, in some examples, comparing the measured potential difference to a plurality of electrocardiographic measurements includes generating a cross-correlation factor between the measured potential difference and each of the stored electrocardiographic measurements of the plurality of stored electrocardiographic measurements. Additionally or alternatively to one or more of the examples disclosed above, in some examples, the method further comprises determining a location on the user's body of the first electrode and a location on the user's body of the second electrode based on the plurality of correlation factors generated.

Although examples of this disclosure have been fully described with reference to the accompanying drawings, it is to be noted that various changes and modifications including, but not limited to, combining features of different examples, omitting a feature or features, etc., as will be apparent to those skilled in the art in light of the present description and figures.

What is claimed is:

1. A device capable of measuring electrocardiographic (ECG) signals, the device comprising:
    a first electrode capable of measuring a first electric potential at a first user location;
    a second electrode capable of measuring a second electric potential at a second user location; and
    a processor capable of
        measuring a potential difference between the first electric potential and the second electric potential to obtain an ECG signal,
        determining whether the first and second electrodes are inverted based on the ECG signal, and
        correcting the ECG signal when the first and second electrodes are determined to be inverted.

2. The device of claim 1, wherein determining whether the first and second electrodes have been inverted comprises determining if a P-wave of the ECG signal exhibits a characteristic indicative of inversion.

3. The device of claim 2, wherein determining whether the first and second electrodes have been inverted further comprises comparing an amplitude of an R-wave of the ECG signal to a maximum of absolute values of amplitudes of a Q-wave and an S-wave of the ECG signal, when an amplitude of the P-wave is lower than a pre-determined threshold.

4. The device of claim 1, wherein the processor is further capable of determining the first user location and the second user location based on the determination of whether the first and second electrodes have been inverted.

5. The device of claim 1, wherein the processor is further capable of correcting the ECG signal by multiplying the ECG signal by −1.

6. A method of detecting and correcting lead inversion in an electrocardiographic (ECG) measurement, the method comprising:
    measuring a potential difference between a first electrode and a second electrode, the first electrode and second electrode being in contact with a user at a first user location and a second user location, respectively, to obtain an ECG signal;
    determining whether the first and second electrodes have been inverted based on the ECG signal; and
    correcting the ECG signal when the first and second electrodes are determined to be inverted.

7. The method of claim 6, wherein determining whether the first and second electrodes have been inverted comprises determining if a P-wave of the ECG signal exhibits a characteristic indicative of inversion.

8. The method of claim 7, wherein determining whether the first and second electrodes have been inverted further comprises comparing an amplitude of an R-wave of the ECG signal to a maximum of absolute values of amplitudes of a Q-wave and an S-wave of the ECG signal, when the amplitude of the P-wave is lower than a pre-determined threshold.

9. The method of claim 6, further comprising determining the first user location and the second user location based on the determination of whether the first electrode and the second electrode have been inverted.

10. The method of claim 6, further comprising correcting the ECG signal by multiplying the ECG signal by −1.

11. A non-transitory computer readable storage medium having stored thereon a set of instructions for detecting and correcting lead inversion in an electrocardiographic (ECG) measurement, that when executed by a processor causes the processor to:

measure a potential difference between a first electrode and a second electrode, the first electrode and second electrode being in contact with a user at a first user location and a second user location, respectively, to obtain an ECG signal;

determining whether the first and second electrodes have been inverted based on the ECG signal; and correcting the ECG signal when the first and second electrodes are determined to be inverted.

12. The non-transitory computer readable storage medium of claim 11, wherein determining whether the first and second electrodes have been inverted comprises determining if a P-wave of the ECG signal exhibits a characteristic indicative of inversion.

13. The non-transitory computer readable storage medium of claim 12, wherein determining whether the first and second electrodes have been inverted further comprises comparing an amplitude of an R-wave of the ECG signal to a maximum of absolute values of amplitudes of a Q-wave and an S-wave of the ECG signal, when the amplitude of the P-wave is lower than a pre-determined threshold.

14. The non-transitory computer readable storage medium of claim 11, the processor being further caused to determine the first user location and the second user location based on the determination of whether the first electrode and the second electrode have been inverted.

15. The non-transitory computer readable storage medium of claim 11, wherein correcting the ECG signal comprises multiplying the ECG signal by −1.

16. A device capable of measuring electrocardiographic signals (ECG), the device comprising:

a first electrode capable of being placed at a first user location;

a second electrode capable of being placed at a second user location; and a processor communicatively couplable to the first and second electrodes and capable of:

determining whether the first electrode and the second electrode have been improperly placed based on an ECG signal obtained from measured differences between the first electrode and the second electrode, and correcting the ECG signal when the first electrode and the second electrode are determined to have been improperly placed.

17. The device of claim 16, wherein determining whether the first electrode and the second electrode have been improperly placed includes comparing the measured differences to a plurality of ECG measurements stored in the device.

18. The device of claim 17, the processor further capable of obtaining the plurality of ECG measurements in an enrollment phase of the device, wherein during the enrollment phase the first electrode and the second electrode are placed in a plurality of known user locations to generate the plurality of ECG measurements.

19. The device of claim 17, wherein comparing the measured differences to the plurality of ECG measurements stored in the device includes generating a cross-correlation factor between the measured differences and each of the ECG measurements stored in the device.

20. The device of claim 19, wherein the processor is further capable of determining the first and second user locations based on the plurality of correlation factors generated.

\* \* \* \* \*